(12) United States Patent
Engler et al.

(10) Patent No.: US 11,400,129 B2
(45) Date of Patent: Aug. 2, 2022

(54) INCREASE IN THE CONTENT OF ESSENTIAL FATTY ACIDS IN EGGS VIA NUTRITIONAL SUPPLEMENTATION OF ANIMALS USING A VERY LOW DOSE OF A FLAVONOID-RICH GRAPE EXTRACT

(71) Applicant: NOR-FEED, Beaucouze (FR)

(72) Inventors: Paul Engler, La Chapelle Saint Laud (FR); David Guilet, Angers (FR)

(73) Assignee: NOR-FEED, Beaucouze (FR)

( * ) Notice: Subject to any disclaimer, the term of this patent is extended or adjusted under 35 U.S.C. 154(b) by 123 days.

(21) Appl. No.: 17/054,159

(22) PCT Filed: May 7, 2019

(86) PCT No.: PCT/FR2019/051043
§ 371 (c)(1),
(2) Date: Nov. 9, 2020

(87) PCT Pub. No.: WO2019/215415
PCT Pub. Date: Nov. 14, 2019

(65) Prior Publication Data
US 2021/0228674 A1      Jul. 29, 2021

(30) Foreign Application Priority Data
May 9, 2018   (FR) ...................................... 1870548

(51) Int. Cl.
| A61K 36/87 | (2006.01) |
| A23K 50/75 | (2016.01) |
| A23K 10/30 | (2016.01) |
| A23L 15/00 | (2016.01) |
| A61K 9/00 | (2006.01) |
| A23K 50/80 | (2016.01) |

(52) U.S. Cl.
CPC .............. *A61K 36/87* (2013.01); *A23K 10/30* (2016.05); *A23K 50/75* (2016.05); *A23K 50/80* (2016.05); *A23L 15/00* (2016.08); *A61K 9/0056* (2013.01); *A23V 2002/00* (2013.01)

(58) Field of Classification Search
CPC ...... A61K 36/87; A61K 9/0056; A23K 50/75; A23K 50/80; A23K 10/30; A23L 15/00; A23V 2002/00
See application file for complete search history.

(56) References Cited

FOREIGN PATENT DOCUMENTS

CN          105685485 A  *  6/2016

OTHER PUBLICATIONS

Magrone, et al., "Administration of a Polyphenol-Enriched Feed to Farmed Sea Bass . . . ," Oxidative Medicine and Cellular Longevity, 2016.
Kangpanich, et al., "Effects of Arachidonic Acid Supplementation in Maturation Diet on Female Reproductive Performance . . . ," PEERJ, vol. 4, Nov. 11, 2016.
Viveros, et al., "Effects of Dietary Polyphenol Rich Grape Products on Intestinal Microflora and Gut Morphology in Broiler Chicks," Poultry Science, vol. 90, No. 3, Mar. 2011.
Kanber, et al., "Effects of Grape Pomace Supplementation to Laying Hen Diet on Performance . . . ," Journal of Applied Animal Research, vol. 44, No. 1, Jan. 2016.
Kangpanich, et al., "Study on Efficiency of Grape Seed Meals Used as Antioxidants in Layer Diets Enriched . . . ," Brazilian Journal of Poultry Science, Apr. 3, 2019.

* cited by examiner

*Primary Examiner* — Aaron J Kosar
(74) *Attorney, Agent, or Firm* — CRGO Global; Steven M. Greenberg

(57) ABSTRACT

Method for modifying the essential fatty acid profile of eggs through low-dose nutritional supplementation based on plant extract rich in flavonoids in the plant extract.
The present invention relates to a method for supplementing animals that produce eggs that are intended for consumption and/or reproduction using a very low dose of plant extract so as to naturally modulate the profile of essential fatty acid in the eggs produced.
Said method consists of a step of supplementing the complete feed and/or the drinking water of the animals using a very low dose of the plant extract and makes it possible to significantly increase the proportion of at least one polyunsaturated fatty acid of the omega-3 family, particularly alpha-linolenic acid (ALA) and/or docosahexaenoic acid (DHA), in the eggs produced by these animals.
The present invention is particularly intended for the agro-feed industry, including the animal nutrition industry, in order to obtain eggs for consumption that are enriched with polyunsaturated fatty acids and/or to improve the quality of eggs intended for reproduction of the species, whether terrestrial and/or aquatic.

10 Claims, No Drawings

INCREASE IN THE CONTENT OF ESSENTIAL FATTY ACIDS IN EGGS VIA NUTRITIONAL SUPPLEMENTATION OF ANIMALS USING A VERY LOW DOSE OF A FLAVONOID-RICH GRAPE EXTRACT

CROSS-REFERENCE TO RELATED APPLICATIONS

This application is a § 371 national phase entry of International Application No. PCT/FR2019/051043, filed May 17, 2019, which claims priority to French Patent Application No. 1870548, filed May 19, 2018.

The present invention relates to the field of the nutrition of egg-producing animals, more particularly feed supplementation with a view to reproduction and/or laying. It relates most particularly to the use of a feed composition comprising at least one plant extract for the purpose of modifying the lipid profile of eggs, fertilized or not, particularly increasing their proportion of at least one polyunsaturated fatty acid (PUFA), particularly from the family of so-called "omega-3" PUFAs.

PRIOR ART

Reproduction is a crucial stage in life. It is based, inter alia, on optimal functioning of gametogenesis for the creation of gametes of excellent quality. Among the qualitative parameters considered, genetic information and the nutritional reserves associated with these gametes are two essential aspects.

Fat is a fundamental part of the nutritional reserves used during embryogenesis. Studies have notably demonstrated the positive impact of certain fatty acids, such as unsaturated fatty acids, on embryonic development in particular (Cherian, 2015).

The most common strategy for modulating the lipid profile of gametes consists in supplementing the diet with raw materials rich in polyunsaturated fatty acids (PUFAs) (Yannakopoulos, 2007). However, this technique entails a greater susceptibility on the part of the feed to oxidize and requires the addition of technological antioxidants in order to guarantee its integrity. These raw materials that are rich in PUFAs also represent an important portion of the feed ration.

The use of an alternative solution that makes it possible to achieve the same ends (increased proportion of PUFAs in the nutritional reserves of gametes) using ingredients that are not susceptible to oxidation and are present in smaller quantities in the ration (less than 200 mg/kg of the complete feed) would optimize the formulation of the feed ration and improve its stability.

Consequently, there remains a need for ingredients that are not susceptible to oxidation and that lead to a modulation of the lipid profile of eggs, and particularly to an increase in the proportion of PUFAs in the nutritional reserves of eggs and, more particularly, of gametes.

Polyphenols are among the substances that have very little susceptibility to oxidation and are known for their antioxidant properties (Williamson & Manach, 2005). Plant extracts rich in polyphenols are used in animal feed to improve the antioxidant status of farm animals. Some plant extracts that are commonly used in animal nutrition for their polyphenol content include extracts of grapes, rosemary, tea, or even turmeric.

On 21 Feb. 2017, the European Commission published a regulation authorizing the use of a grape extract as an additive for animal feed within the European Union (Implementing Regulation 2017/307). Said extract comprises at least 80% total polyphenols expressed as catechin equivalent and at least 60% proanthocyanidins, belonging to the flavonoid family. It also contains at least 0.75% anthocyanins and anthocyanidins. The recommended dose for use is 5 to 100 grams of the grape extract per tonne of complete feed distributed to the animal ('Official Journal L 44/2017', n.d.).

The authors of the present invention have shown that the use of at least one particular grape extract makes it possible to resolve all or part of the problems mentioned above.

SUMMARY OF THE INVENTION

The present invention therefore relates to the use of at least one grape extract, said at least one grape extract comprising:
  from 50 to 95% by weight, preferably 65 to 85% total polyphenols, most preferably 80 to 85%, expressed as catechin equivalent, relative to the total weight of the extract,
  from 30% to 90% by weight, preferably 50 to 70% proanthocyanidins, most preferably 60 to 70% relative to the total weight of the extract,
  from 0.5 to 10% by weight, preferably 0.5 to 2%, most preferably 0.75 to 2% total anthocyanins and anthocyanidins relative to the total weight of the extract,
  for the purpose of modifying the lipid profile of eggs in an animal that has been supplemented with said at least one grape extract, selected from the group consisting of oviparous and ovoviviparous animals, particularly fish and poultry.

The term "supplemented animal" is understood to refer to an animal that has consumed the feed composition comprising said at least one grape extract according to the invention.

The term "non-supplemented animal" is understood to refer to an animal that has consumed a feed composition not comprising said at least one grape extract according to the invention.

As already mentioned, said at least one grape extract used according to the invention is weakly susceptible to oxidation, or even not susceptible to oxidation. Consequently, it can be used to obtain a feed composition that is stable in terms of oxidation without the addition of antioxidants. More particularly, said at least one grape extract does not require the additional supplementation of at least one of the compounds selected from the group consisting of technological antioxidants, including, in particular, ethoxyquin, butylated hydroxyanisole (BHA) or butylated hydroxytoluene (BHT).

In addition, said at least one grape extract used according to the invention makes it possible to increase the level of at least one polyunsaturated fatty acid, particularly of at least one polyunsaturated fatty acid from the family of so-called "omega-3" polyunsaturated fatty acids, in the eggs of animals whose diet has been supplemented with this extract, notably alpha linolenic acid and/or docosahexaenoic acid, particularly docosahexaenoic acid, relative to eggs from animals not supplemented with said at least one grape extract. The use of said at least one grape extract according to the invention causes in particular an increase of at least 10% in at least one polyunsaturated fatty acid, particularly of the family of so-called "omega-3" polyunsaturated fatty acids, in the eggs of said supplemented animal, preferably at least 15% and most preferably at least 20% by weight relative to the weight of the polyunsaturated fatty acids in the eggs of said animal that has not been supplemented with said at least one grape extract according to the invention.

The term "polyunsaturated fatty acid" is understood to refer to a fatty acid of which the carbon chain comprises a plurality of unsaturated carbon-carbon bonds.

The term "polyunsaturated fatty acid of the family of so-called "omega-3" polyunsaturated fatty acids" is understood to refer to fatty acids of which the carbon chain comprises a plurality of unsaturated carbon-carbon bonds and of which the first double bond of the carbon chain of the acid, counting from the end opposite the carboxyl, is located on the third carbon-carbon bond.

Another advantage of the invention is that it makes it possible to eliminate or at least reduce the amount of ingredients conventionally used in animal feed compositions, such as antioxidant agents and polyunsaturated fatty acid(s), and thus to reduce the production costs and also the environmental impact of these compositions.

Yet another advantage of the invention is that the grape extract can be used in the feed composition according to the invention in generally very low amounts, i.e. in doses less than or equal to 200 ppm, preferably less than or equal to 100 ppm, which makes it possible to optimize the formulation of the feed composition.

Other subject matter, aspects, advantages and properties of the present invention are presented in the detailed description and the examples that follow.

DETAILED DESCRIPTION

Grape Extract.

The term "grape extract" is understood to refer to an extract from the botanical genus (*Vitis*), and particularly *Vitis vinifera* and/or *Vitis labrusca* and/or *Vitis riparia* and/or *Vitis rupestris* and/or *Vitis berlandieri* and/or *Vitis amurensis* and/or *Vitis coignetiae* and/or *Vitis vulpina* and/or *Vitis acerifolia* and/or *Vitis aestivalis* and/or *Vitis rotundifolia*, preferably *Vitis vinifera*.

An element of the structure of a plant selected particularly from the group consisting of berries, seeds and skins or mixtures thereof are used to prepare the grape extract used in the invention. Preferably, grape skins and/or seeds are used, very preferably grape skins and seeds.

As already mentioned, said at least one grape extract which can be used according to the invention comprises:

from 50 to 95% by weight, preferably 65 to 85% total polyphenols, most preferably 80 to 85%, expressed as catechin equivalent, relative to the total weight of the extract, from 30% to 90% by weight, preferably 50 to 70% proanthocyanidins, most preferably 60 to 70% relative to the total weight of the extract, from 0.5 to 10% by weight, preferably 0.5 to 2%, most preferably 0.75 to 2% total anthocyanins and anthocyanidins relative to the total weight of the extract.

The term "polyphenols" is understood to refer to natural chemical compounds that are characterized by the presence of at least two phenolic groups which form more or less complex structures. They include, inter alia, constituents of the subgroup of flavonoids, which includes, in particular, proanthocyanidins, anthocyanins and anthocyanidins.

The term "proanthocyanidin" is understood to refer to polymers of catechins.

They are made up of catechin units linked together by carbon-carbon bonds of the 4→8 or 4→6 type.

The term "anthocyanidin" is understood to refer to natural pigments based on the structure of the flavylium ion (2-phenylchromenylium ion).

The term "anthocyanin" is understood to refer to the heteroside derivatives of the anthocyanidins.

Method of Preparation

Preferably, the method for obtaining the grape extract as described in the invention consists in carrying out a grape extraction (depulped whole berry of *Vitis vinifera*) using non-synthetic solvents, followed by a purification and then atomization of the extract, or in homogeneously mixing at least one dry extract of grape skin containing at least 1% of anthocyanins and total anthocyanidins with at least one dry extract of grape seeds containing at least 1% total flavonoids. The production method yields a composition containing:

from 50 to 95% by weight, preferably 65 to 85% total polyphenols, most preferably 80 to 85%, expressed as catechin equivalent, relative to the total weight of the extract, from 30% to 90% by weight, preferably 50 to 70% proanthocyanidins, most preferably 60 to 70% relative to the total weight of the extract, and from 0.5 to 10% by weight, preferably 0.5 to 2%, most preferably 0.75 to 2% total anthocyanins and anthocyanidins relative to the total weight of the extract, in particular so as to obtain an extract that complies with the regulation authorizing the use of a grape extract as an additive for animal feed within the European Union (Implementing Regulation 2017/307).

Of course, the production method should preferably comply with good production practices.

Feed Composition

The invention also relates to the use of at least one grape extract according to the invention in a feed composition, said at least one grape extract being included in a feed composition.

Advantageously, the use of the grape extract according to the invention does not require any additional supplementation of technological antioxidant in the feed composition relative to a feed composition not supplemented with a grape extract according to the invention.

The feed composition can further comprise a physiologically acceptable vehicle that is suitable for oral use.

According to a first embodiment, the feed composition is in solid form, preferably selected from the group consisting of a powder, a granule, a tablet, and an extruded or non-extruded pellet.

When the feed composition is in solid form, the amount of grape extract is between 1 and 200 mg/kg, preferably between 5 and 100 mg/kg in the dry composition, and so the amount of grape extract ranges from $1 \times 10^{-4}\%$ to $2 \times 10^{-2}\%$ by weight, preferably from $2.5 \times 10^{-4}\%$ to $5 \times 10^{-1}\%$ by weight relative to the total weight of the dry extract of the feed composition.

According to another embodiment, the feed composition is in liquid form, preferably selected from the group consisting of a suspension, a solution, and a drinking water.

When the feed composition is in liquid form, the amount of grape extract is between 1 and 100 mg/L, preferably between 2.5 and 50 mg/L, and so the amount of grape extract ranges from $1 \times 10^{-4}\%$ to $1 \times 10^{-2}\%$, preferably from $2.5 \times 10^{-4}\%$ to $5 \times 10^{-1}\%$ by weight relative to the total weight of the feed composition.

The feed composition therefore comprises a very low dose of grape extract.

The feed composition according to the invention generally comprises at least one excipient selected from the group consisting of zootechnical additives and technological additives.

The preparation of the feed composition used according to the invention implements conventional methods that form part of the general skills of those skilled in the art.

The feed composition used according to the invention can be particularly in the form of an additive, a raw material, or a compound feed.

The term "compound feed" is understood to refer to a mixture of at least two raw materials for foodstuffs for animals, comprising or not comprising additives for animal feed, that is intended for use as oral animal feed in the form of complete feed or complementary feed (Regulation 767/2009).

The term "raw material" is understood to refer to all fresh or preserved products of plant or animal origin, in the natural state, that are derived from industrial processing thereof, as well as to organic or inorganic substances, comprising or not comprising additives, that are intended to be used for oral feeding of animals, either directly as such or after processing, for the preparation of compound feeds for animals, or as carriers for premixtures (Council Directive 96/25/EC of 29 Apr. 1996).

The feed composition according to the present invention can be used directly as feed, in which case it can be considered as a "raw material" in the preparation of said compound feed.

The term "additive" is understood to refer to all substances, microorganisms or preparations, other than the raw materials for foodstuff for animals and premixtures, that are deliberately added to animal feed or to water in order to fulfill one or more of the following functions in particular: to meet the nutritional needs of animals, to have a positive effect on the characteristics of the animal feed or products of animal origin, on the color of ornamental fish or birds, on the environmental consequences of animal production, on production, animal performance or welfare, or to have a coccidiostatic or histomonostatic effect (EU Regulation 1831/2003).

Uses

The present invention relates to the use of at least one grape extract according to the invention or of a feed composition containing at least one grape extract according to the invention for the purpose of modifying the lipid profile of eggs in an animal selected from the group consisting of oviparous and ovoviviparous animals, particularly fish and poultry.

Within the meaning of the present invention, the term "oviparous" is understood to refer to an animal that reproduces by eggs laid before or after fertilization but before hatching. This definition applies, for example, to a fish that lays eggs that are fertilized externally. The female lays the eggs, which are fertilized in water by the male. Embryonic growth will be completed outside the maternal organism. The eggs then hatch, and the time prior to hatching varies depending on the fish and the temperature.

Within the meaning of the present invention, the term "ovoviviparous" is understood to refer to an animal that reproduces by means of eggs but keeps them in its genital tract until the hatching of the young, the embryo developing only from the reserves accumulated in the egg. This definition applies, for example, to a fish that carries eggs that incubate and hatch in the womb of the mother without a nutritional relationship therewith (simple exchanges of water and gas). The ovoviviparous embryo feeds in the egg and hatches just before birth.

In the context of the present invention, said at least one grape extract is used in an adult animal, i.e. one that has reached its sexual maturity and is capable of reproducing, preferably for a period ranging from 2 weeks to 8 months.

Advantageously, the modification of the lipid profile of the eggs consists in inducing, in the eggs of said animal that has been supplemented with said at least one grape extract according to the invention, an increase in the level of at least one polyunsaturated fatty acid, more particularly of the level of at least one fatty acid from the family of so-called "omega-3" polyunsaturated fatty acids (relative to the eggs of said animal that has not been supplemented with said at least one grape extract according to the invention). Advantageously, said at least one polyunsaturated fatty acid of the omega-3 family (PUFAs) of which the level is increased is alpha-linolenic acid (ALA) and/or docosahexaenoic acid (DHA), very particularly docosahexaenoic acid (DHA).

Generally, the level of at least one polyunsaturated fatty acid in the eggs of said animal that has been supplemented with said at least one grape extract according to the invention is increased by at least 10%, preferably by at least 15%, and most preferably by at least 20% by weight relative to the weight of polyunsaturated fatty acids in the eggs of said animal that has not been supplemented with said at least one grape extract.

Therefore, according to the invention, the use of said at least one grape extract according to the invention at a very low dose in the diet of an egg-producing animal makes it possible to achieve a significant increase in the level of at least one polyunsaturated fatty acid in the eggs of said supplemented animal, particularly a significant increase in the level of ALA and/or DHA, most particularly in the level of DHA.

According to a first variant, the eggs obtained by the implementation of the present invention are unfertilized; these are eggs enriched with unsaturated fatty acid(s) intended for human consumption.

According to a second variant, the eggs obtained by the implementation of the present invention are fertilized; these are eggs intended for reproduction that have optimized nutritional reserves.

The examples that follow aim to illustrate the invention without limiting its scope.

EXAMPLES

Exemplary embodiments of the invention. Examples 1 and 2 show embodiments of the invention in two species of fish, and example 3 shows an embodiment of the invention in one species of poultry.

Example 1: Modulation of the Fatty Acid Profile in the Eggs of Rainbow Trout (*Oncorhynchus mykiss*)

Two feeds were tested, differing only by the presence of 60 ppm of grape extract in the feed of the "supplemented" group. The feed consisted of fishmeal, skinned field beans, wheat gluten, cooked soybean meal, fish oils, wheat, corn gluten, rapeseed oil, rapeseed meal, minerals, vitamins.

Composition of the feeds of the two groups.

TABLE 1

| Group | Control (CTL) | Supplemented (NG) |
|---|---|---|
| Proteins (%) | 39 | 39 |
| Lipids (%) | 27 | 27 |
| of which omega-3 (in % of lipids) | 15.5 | 15.5 |
| Cellulose (%) | 1.7 | 1.7 |
| Ash (%) | 7 | 7 |
| Grape extract according to the invention (mg/kg) | 0 | 60 |

Each group consisted of 130 rainbow trout spawners, each comprising two pools of 40 females and one pool of 50 males. Fish of the same sex were randomly distributed between the two groups.

All the basins were supplied by the same water circuit, and the water quality thereof was monitored and checked daily.

The supplementation trial was conducted over the 5-month period preceding spawning.

The eggs of the females were then harvested and stored at −80° C. until analysis.

Ten egg samples from each group underwent the following preparation protocol:
Lyophilization of 10 g of fresh eggs,
Automatic pressurized extraction of 2 g of egg lyophilizate using dichloromethane (DCM),
Dry evaporation of the liquid extracts obtained,
Saponification of 50 mg of dry extract
Derivatization using BSTFA (N,O-bis-trimethylsilyl-trifluoroacetamide),
GC-MS injection.

The area under the curve of the DHA peaks was then integrated automatically in order to allow a statistical comparison of the results using the statistical t-test (Welch, R software, v3.4.1).

Results of the integration of DHA peaks from rainbow trout eggs and associated statistical analysis.

TABLE 2

| Group | CTL | NG |
|---|---|---|
| Area under the DHA peak curve (mUA) | 32861606 | 40507107 |

The results of the analysis of rainbow trout eggs thus demonstrated a significant increase in the proportion by weight of DHA in the eggs of fish that had been supplemented with grape extract (+23.3%, $p<0.05$).

Example 2: Modulation of the Fatty Acid Profile in the Eggs of Mullet (*Mugil cephalus*)

Two feeds were tested, differing by the presence of 100 ppm of grape extract in the feed of the supplemented group ("NG"). The feed consisted of fishmeal, wheat gluten, cooked soybean meal, corn gluten, fish oils, vitamins, minerals.

Composition of the feeds of the two groups.

TABLE 3

| Group | Control (CTL) | Supplemented (NG) |
|---|---|---|
| Protein (%) | 34.2 | 35.6 |
| Lipids (%) | 9.1 | 9.5 |
| of which omega-3 (in % of lipids) | 7.7 | 6.6 |
| Ash (%) | 9.1 | 8.0 |
| Grape extract according to the invention (mg/kg) | 0 | 100 |

Each group was made up of 5,000 sexually mature (3-year-old) mullets (unsexed) randomly distributed to outdoor rearing ponds.

The fish were fed for 3 months before the ovaries were harvested.

At the end of the rearing phase, an analysis of the fatty acid profiles was carried out on a mixture of ovaries of 10 fish per group according to the following protocol:
Folch extraction (Folch et al. 1957)
Saponification
Transmethylation (ISO standard 12966),
GC-MS analysis.

The results were then integrated automatically in order to define the relative proportion of various fatty acids in the lipid profile of mullet ovaries.

Results of the integration of DHA peaks from rainbow trout eggs.

TABLE 4

| Group | CTL | NG |
|---|---|---|
| Relative proportion of DHA (% of total fatty acids) | 5.71% | 6.52% |

The results of the analysis of mullet ovaries thus demonstrated an increase in the proportion by weight of DHA in the ovaries of fish that had been supplemented with grape extract (+14.2%).

Example 3: Modulation of the Fatty Acid Profile in the Eggs of Laying Hens (*Gallus gallus domesticus*)

Two feeds were tested, differing only by the presence of 30 ppm of grape extract in the feed of the supplemented group ("NG"). The feed consisted of wheat, corn, soybean meal, sunflower meal, calcium carbonate, rapeseed meal, minerals, vitamins, amino acids.

Composition of the feeds of the two groups.

TABLE 5

| Group | Control (CTL) | Supplemented (NG) |
|---|---|---|
| Protein (%) | 15.5 | 15.5 |
| Lipids (%) | 2.9 | 2.9 |
| Cellulose (%) | 4.6 | 4.6 |
| Ash (%) | 12.1 | 12.1 |
| Grape extract according to the invention (mg/kg) | 0 | 30 |

Each group consisted of 286 hens, divided into 11 cages of 26 hens, distributed randomly in the same battery.

The supplementation period was 5 weeks of feeding. Four eggs per cage were harvested on the first and last day of the trial for both groups. They then underwent the following protocol:

Separation of yolks,
Homogenization of 4 egg yolks per cage,
Lyophilization of the yolks,
Folch extraction (Folch et al., 1957) on 200 mg of lyophylizate
Evaporation of the liquid extract obtained,
Transmethylation of the dry extract (ISO standard 12966), GC-MS analysis.

The area under the curve of the DHA peaks was then integrated automatically in order to allow a statistical comparison of the results using the statistical t-test (Welch, R software, v3.4.1).

Results of the integration of DHA peaks from rainbow trout eggs and associated statistical analysis.

TABLE 6

| Group | CTL | NG |
|---|---|---|
| Area under the DHA peak curve (mUA) | 28636531 | 34651862 |

The results of the analysis of chicken eggs thus demonstrated a significant increase in the proportion by weight of DHA in the poultry eggs that had been supplemented with grape extract (+21.0%, p<0.05).

REFERENCES

Cherian, G. (2015). Nutrition and metabolism in poultry: role of lipids in early diet. Journal of Animal Science and Biotechnology, 6, 28. https://doi.org/10.1186/s40104-015-0029-9

Folch, J., Lees, M., & Sloane Stanley, G. H. (1957). A simple method for the isolation and purification of total lipids from animal tissues. The Journal of Biological Chemistry, 226 (1), 497-509.

Official Journal L 44/2017. (n.d.). Retrieved 20 Mar. 2018, from http://eurlex.europa.eu/legal-content/FR/TXT/HTML/?uri=OJ1:2017:044:FULL&from=FR Williamson, G., & Manach, C. (2005). Bioavailability and bioefficacy of polyphenols in humans. II. Review of 93 intervention studies. The American Journal of Clinical Nutrition, 81(1), 243S-255S.

Yannakopoulos, A. L. (2007). Egg enrichment in omega-3 fatty acids. In Bioactive Egg Compounds (pp. 159-170). https://doi.org/10.1007/978-3-540-37885-3_20

The invention claimed is:

1. A grape extract supplementation method, comprising: modifying a lipid profile of eggs in an animal selected from the group consisting of oviparous and ovoviviparous animals, by supplementing the animal with a grape extract comprising:
   a) from 50 to 95% by weight, total polyphenols expressed as catechin equivalent, relative to the total weight of the extract,
   b) from 30% to 90% by weight, proanthocyanidins relative to the total weight of the extract,
   c) from 0.5 to 10% by weight, total anthocyanins and anthocyanidins relative to the total weight of the extract.

2. The method according to claim 1, wherein the supplementation of the animal increases the level of at least one polyunsaturated fatty acid in the eggs of said supplemented animal, more particularly the level of at least one polyunsaturated fatty acid of the family of omega-3 polyunsaturated fatty acids, relative to the eggs of said animal that has not been supplemented with said at least one grape extract.

3. The method according to claim 1, wherein said at least one polyunsaturated fatty acid is alpha-linolenic acid and/or docosahexaenoic acid.

4. The method according to claim 1, wherein the level of at least one polyunsaturated fatty acid in the eggs of said supplemented animal is increased by at least 10%, by weight relative to the weight of the polyunsaturated fatty acids in the eggs of said animal that has not been supplemented with said at least one grape extract.

5. The method according to claim 1, said at least one grape extract being included in a feed composition, said feed composition being an additive, a feed, a raw material, or a complementary feed.

6. The method according to claim 5, wherein said feed composition is in solid form.

7. The method according to claim 6, wherein the amount of grape extract ranges from $1\times10^{-4}$% to $2\times10^{-2}$%, by weight relative to the total weight of the dry extract of the feed composition.

8. The method according to claim 5, wherein the feed composition is in liquid form.

9. The method according to claim 8, wherein the amount of grape extract ranges from $1\times10^{-4}$% to $1\times10^{-2}$%, by weight relative to the total weight of the feed composition.

10. The method according to claim 1, wherein the eggs are intended for human consumption or for reproduction.

* * * * *